United States Patent [19]

Swaile

[11] Patent Number: 6,083,493
[45] Date of Patent: *Jul. 4, 2000

[54] ANTIPERSPIRANT COMPOSITIONS CONTAINING ISOPROPYL GLYCEROL ETHER

[75] Inventor: David Frederick Swaile, Cincinnati, Ohio

[73] Assignee: The Procter & Gamble Company, Cincinnati, Ohio

[ * ] Notice: This patent is subject to a terminal disclaimer.

[21] Appl. No.: 09/379,713

[22] Filed: Aug. 24, 1999

[51] Int. Cl.⁷ ............... A61K 7/32; A61K 7/36; A61K 7/38; A61K 7/00
[52] U.S. Cl. ............... 424/65; 424/66; 424/67; 424/68; 424/400; 424/401
[58] Field of Search ............... 424/65, 66, 67, 424/68, 400, 401

[56] References Cited

U.S. PATENT DOCUMENTS

| | | | |
|---|---|---|---|
| 3,420,932 | 1/1969 | Jones et al. | 424/47 |
| 3,904,741 | 9/1975 | Jones et al. | 423/462 |
| 3,928,545 | 12/1975 | Jones et al. | 423/463 |
| 4,435,382 | 3/1984 | Shin et al. | 424/66 |
| 4,704,271 | 11/1987 | Hourihan et al. | 424/66 |
| 4,719,102 | 1/1988 | Randhawa et al. | 424/66 |
| 4,720,381 | 1/1988 | Schamper et al. | 424/66 |
| 4,767,875 | 8/1988 | Vincenti et al. | 556/175 |
| 4,781,917 | 11/1988 | Luebbe et al. | 424/65 |
| 5,179,220 | 1/1993 | Katsoulis et al. | 556/27 |
| 5,486,347 | 1/1996 | Callaghan et al. | 423/623 |
| 5,643,558 | 7/1997 | Provancal et al. | 424/66 |

FOREIGN PATENT DOCUMENTS

| | | |
|---|---|---|
| 0 007 191 A1 | 1/1980 | European Pat. Off. . |
| 0 183 171 A2 | 6/1986 | European Pat. Off. . |
| 0 191 628 A2 | 8/1986 | European Pat. Off. . |
| 2 048 229 | 12/1980 | United Kingdom . |
| WO 96/33800 | 10/1996 | WIPO . |
| WO 97/34577 | 9/1997 | WIPO . |
| WO 98/58626 | 12/1998 | WIPO . |

*Primary Examiner*—Shelley A. Dodson
*Attorney, Agent, or Firm*—William J. Winter

[57] ABSTRACT

The present invention is directed to antiperspirant compositions which comprise from about 0.1% to about 99.9% by weight of solubilized or solid antiperspirant active and from about 0.1% to about 99.9% by weight of a carrier which comprises isopropyl glycerol ether, preferably in combination with a volatile silicone liquid carrier and dimethiconol as a coupling agent. The isopropyl glycerol ether carrier is a highly effective coupling agent and is milder to the skin when applied topically to the axilla or other areas of the skin as compared to many other polyol-containing carriers. Preferred are antiperspirant compositions containing solubilized antiperspirant active.

39 Claims, No Drawings

ANTIPERSPIRANT COMPOSITIONS CONTAINING ISOPROPYL GLYCEROL ETHER

FIELD OF INVENTION

This invention relates to antiperspirant compositions comprising antiperspirant active and a carrier comprising isopropyl glycerol ether. This carrier is milder to the skin than many other polyol-containing carriers, and is especially effective as a coupling agent for gellant systems containing silicone carriers.

BACKGROUND OF THE INVENTION

Polyol-containing carriers and solvents are well known for use in deodorant and antiperspirant compositions. These carriers are most typically used to solubilize the antiperspirant active, or as coupling agents during the manufacturing process. These polyol carriers are typically aliphatic polyhydric alcohols which have from 2 to 12 carbon atoms, examples of which include ethylene glycol, diethylene glycol, butylene glycol, 1,2-proplyene glycol, 1,3-propylene glycol, 1,3-butylene glycol (1,3-butane-diol), glycerine (1,2,3-trihydroxy propane), 2-methyl-2,4-pentane-diol (hexylene glycol), 2-ethyl-1,3-hexane-diol, 1,2,6-hexanetriol, and combinations thereof.

Polyol-containing carriers are especially useful in formulating a variety of consumer products containing solubilized antiperspirant active. In making such products, the polyol-containing carrier is typically in the form of an aqueous system which is used to initially solubilize the antiperspirant active. Once the antiperspirant active is solubilized, the water in the aqueous system is removed by any of a variety of known means. The anhydrous solution is then used to formulate an antiperspirant composition containing solubilized antiperspirant active.

Polyol-containing carriers are especially useful in formulating clear or translucent antiperspirant compositions. These compositions are typically anhydrous systems containing solubilized antiperspirant active, wherein the polyol carrier is used to help solubilize the active and in most cases provides the primary carrier material within which the solubilized active is miscible or dispersed within.

Many polyol-containing carriers, however, can cause skin irritation when topically applied to the underarms or other sensitive areas of the skin. This skin irritation is especially problematic when the applied composition is an anhydrous system containing higher concentrations of the polyol carrier. These higher polyol concentrations are often necessary in anhydrous antiperspirant compositions to successfully couple product gellants, structurants, thickening agents or other similar materials with other product carriers or solvents. This skin irritation, especially when caused by higher polyol concentrations, is especially problematic in a small percentage of the population that is unusually sensitive to topical polyol irritation. Although this type skin irritation can be minimized by adding lower irritation solvents such as mineral oil or volatile silicones, these low irritation solvents are not miscible with higher concentrations of most high-polarity polyol solvents.

It has now been found that polyol-containing carriers, and in particular isopropyl glycerol ether containing carriers, can be formulated which cause remarkably less skin irritation. It has been found that isopropyl glycerol ether is an excellent coupling agent that not only causes less skin irritation, but that can be used at lower concentrations which further results in reduced skin irritation.

It is therefore an object of the present invention to provide a polyol-containing antiperspirant composition that is milder to the skin, and further to provide such a composition that also has good skin feel characteristics during and after topical application.

SUMMARY OF THE INVENTION

The present invention is directed to antiperspirant compositions comprising from about 0.1% to about 99.9% by weight of antiperspirant active and from about 0.1% to about 99.9% by weight of a carrier comprising isopropyl glycerol ether. The antiperspirant active may be solubilized or in the form of a particulate solid.

It has now been found that the selection of isopropyl glycerol ether as a solvent or coupling agent in an antiperspirant composition provides the composition with improved performance relative to most polyol-containing solvents known for use in antiperspirant compositions. In particular, this select polyol is milder to the skin than many other similar polyol-containing solvents. As compared to other diol solvents, isopropyl glycerol ether is especially effective as a coupling agent in antiperspirant compositions, especially those compositions that comprise a solid gellant and a volatile silicone solvent. The isopropyl glycerol ether solvent is especially effective at coupling the solid gellant and the volatile silicone solvent into a single phase system.

It has also been found that the antiperspirant compositions of the present invention provide improved skin feel performance, aesthetics, and/or product stability as compared to other polyol-containing antiperspirant compositions.

DETAILED DESCRIPTION

The antiperspirant compositions of the present invention include antiperspirant compositions in final or intermediate product form, and include product forms such as solids or gel solid sticks, soft solids or creams, lotions or other liquids, aerosol or pump sprays, and so forth. These antiperspirant compositions are intended for topical application to the underarm or other suitable areas of the skin, or as manufacturing intermediates.

The term "ambient conditions" as used herein refers to surrounding conditions under about one atmosphere of pressure, at about 50% relative humidity, and at about 25° C.

The term "volatile" as used herein refers to those materials which have a measurable vapor pressure as measured at 25° C. Such vapor pressures will typically range from about 0.01 mmHg to about 6 mmHg, more typically from about 0.02 mmHg to about 1.5 mmHg, and have an average boiling point at one atmosphere of pressure (1 atm) typically less than about 250° C., more typically less than about 235° C., at 1 atmosphere (atm) of pressure.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The antiperspirant compositions of the present invention can comprise, consist of, or consist essentially of the essential elements and limitations of the invention described herein, as well as any of the additional or optional ingredients, components, or limitations described herein.

Liquid Carrier

The antiperspirant compositions of the present invention comprises from about 0.1% to about 99.9% by weight of a liquid carrier comprising isopropyl glycerol ether, preferably a liquid carrier comprising a combination of isopropyl glycerol ether and one or more other known or otherwise effective liquid carrier materials. The carrier is a liquid under ambient conditions, and therefore includes carrier liquid combinations or combinations of carrier liquids and dissolved carrier solids, provided that any such combination is in liquid form under ambient conditions.

The antiperspirant compositions of the present invention may be formulated as an aqeuous or anhydrous composition. For an aqueous formulation, the antiperspirant compositions may further comprise from about 10% to about 75% by weight of water, preferably from about 10% to about 60% by weight of water, even more preferably from about 20% to about 50%, by weight of water. For an anhydrous formulation, antiperspirant compositions contain less than about 20%, more preferably less than about 5%, even more preferably less than about 3%, even more preferably less than about 1%, most preferably zero percent, by weight of free or added water.

The concentration of isopropyl glycerol ether in the antiperspirant composition of the present invention ranges from about 0.1% to about 99.9% by weight of the antiperspirant composition, but specific isopropyl glycerol ether concentrations may vary greatly depending upon variables such as 1) the function to be served by the isopropyl glycerol ether, 2) the desired product form, viscosity, and hardness of the antiperspirant composition, 3) whether the antiperspirant composition is in final or intermediate form, and 4) other formulation variables well know in the chemical or formulation arts. For most product forms, the concentration of isopropyl glycerol ether in the antiperspirant composition ranges from about 0.1% to about 70%, more preferably from about 1% to about 40%, even more preferably from about 5% to about 25%, by weight of the composition.

In addition to the isopropyl glycerol ether carrier, the antiperspirant composition may further comprise one or more optional liquid carriers suitable for topical application and appropriate for the product form desired. Such other optional carriers include any known or otherwise effective liquid carrier material for use in antiperspirants, deodorants or other topical compositions. In the event that the optional liquid carrier is not readily miscible or dispersible in isopropyl glycerol ether or other materials in the liquid carrier component, then other liquid carriers or coupling agents may be added to the composition to bring the isopropyl glycerol ether and other immiscible or nondispersible materials (e.g., nonpolar solvents) into a homogenous solution or dispersion. In this context, it has been found that silicone containing carriers or coupling agents, especially silicone carriers having one or more hydroxyl groups, e.g., dimethiconols as described hereinafter, are especially useful as additional liquid carriers or coupling agents.

The antiperspirant composition of the present invention is preferably anhydrous. In this context, the term "anhydrous" means that the composition contains less than about 10%, more preferably less than about 5%, even more preferably less than about 3%, even more preferably less than about 1%, most preferably zero percent, by weight of free or added water, excluding any water of hydration typically associated with antiperspirant active when formulated in the form of particulate solids, and excluding any water of hydration typically associated with any other added solids.

The preferred concentration of liquid carriers in the antiperspirant composition will vary with the selected product form. In this context, the term "liquid carriers" refers to the combination of isopropyl glycerol ether and any optional carrier liquids. For most product forms, including solid sticks or soft solid sticks or creams, liquid carrier concentrations preferably range from about 10% to about 90%, more preferably from about 30% to about 70%, even more preferably from about 45% to about 70%, by weight of the antiperspirant composition. For aerosol concentrates, pump sprays, roll-on and other liquid product forms, the liquid carrier concentration preferably ranges from about 50% to about 99%, more preferably from about 60% to about 98%, even more preferably from about 75% to about 98%, by weight of the composition. Aerosol concentrates may further comprise a propellant to form the desired aerosol spray product.

The antiperspirant compositions of the present invention include final and intermediate product forms, and such forms can have a wide range of viscosity and physical characteristics depending on whether the product form is a solid, soft sold, cream, lotion, aerosol, pump spray, and so forth.

Optional liquid carriers for use in combination with isopropyl glycerol ether in the antiperspirant composition of the present invention includes any topically safe and effective organic, silicone-containing or fluorine-containing, volatile or non-volatile, polar or non-polar carrier liquid, provided that the resulting combination of carrier materials form a solution or other homogenous liquid or liquid dispersion at the selected processing temperature of the composition. Processing temperatures for the antiperspirant compositions typically range from about 28° C. to about 250° C., more typically from about 28° C. to about 110° C., and even more typically from about 28° C. to about 100° C.

The antiperspirant composition of the present invention preferably further comprises dimethiconol as an optional liquid carrier. Preferred concentrations of the dimethiconol range from about 0.1% to about 50%, more preferably from about 1% to about 35%, even more preferably from about 2% to about 20%, by weight of the composition. Dimethiconols suitable for use as the preferred optional liquid carrier include those corresponding to the formula:

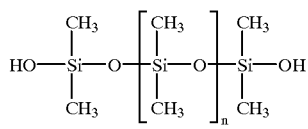

wherein n is number having a value of zero or greater, preferably from about 1 to about 100, more preferably from about 1 to about 50, even more preferably from about 1 to about 10. Nonlimiting examples of suitable dimethiconols include Masil® SFR 70, Mazol® SFR 18,000, Mazol® SFR 50,000, Mazol® SFR 100, Mazol® SFR 150,000, Mazol® SFR 750, Mazol® SFR 2000, and Mazol® SFR 3500, all available from PPG/Specialty Chemicals; and Unisil SF-R available from Universal Preservative. Other available dimethiconols include Abil® OSW 12, OSW13, Abil® OSW 15, and Abil® CK, all available from Goldschmidt; Dow Corning® 1401 Fluid, Dow Corning® Q2-1403 Fluid both available from Dow Corning, and Tri-Sil HGC 5000 available from Tri-K Industries.

Other preferred but optional liquid carriers include PPG-3-myristyl ether, diisopropyl adipate, PPG-14 butyl ether, dimethicone copolyols, and combinations thereof, especially in combination with a dimethiconol as described above.

Other optional liquid carriers include modified or organofunctional silicone carriers such as polyalkylsiloxanes, polyalkyarylsiloxanes, polyestersiloxanes, polyethersiloxane copolymers, polyfluorosiloxanes, polyaminosiloxanes, and combinations thereof. These modified silicone carriers are typically liquid under ambient conditions, and have a preferred viscosity of less than about 100,000 centistokes, more preferably less than about 500 centistokes, even more preferably from about 1 centistoke to about 50 centistokes, and most more preferably from about 1 centistoke to about 20 centistokes. These modified silicone carriers are generally known in the chemical arts, some examples of which are described in 1 Cosmetics, Science and Technology 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Suitable modified silicone carriers include, but are not limited to, compounds or materials such as those defined hereinabove and which are generally characterized as follows: silicone polyethers or silicone glycols (such as dimethicone copolyol); silicone alkyl-linked polyethers (such as Goldschmidt EM-90 or EM-97); siloxane surfactants of a pendant/rake/comb configuration, silicone surfactants of a trisiloxane configuration, and silicone surfactants of an ABA/alpha-omega block copolymers (such as polyoxyalkylenes, polyoxyethylene or ethoxylated, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, alkyl, methyl, amino, trifluoropropyl, vinyl, alkoxy, arylalkyl, aryl, phenyl, styryl, polyethers, esters, carboxylics; alkylmethyl siloxanes or silicone waxes (such as hexyl, octyl, lauryl, cetyl, stearyl); nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxmethoxytrisiloxane; silicone emulsifiers; silicone or siloxane resins, alkyl silicone resins, polyoxyalkylene silicone resins; MQ Resins such as Shiseido/Shin-etsu ,e.g. Japanese Patent Publication JP86143760 or from Walker Chem. 6MBH (described in EP722970); alkoxysiloxanes; alkoxysilanes; methicones (polymethylalkylsiloxanes); and combinations thereof.

Nonlimiting examples of suitable modified silicone carriers for use in the antiperspirant compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520-US Emulsion; DC-593 Fluid (Dimethicone [and] Trimethylsiloxysilicate); DC-3225C Fluid (Cyclomethicone [and] Dimethicone Copolyol); DC-190 Fluid (Dimethicone Copolyol); DC-193 Fluid (Dimethicone Copolyol); DC-1401 (Cyclomethicone [and] Dimethiconol); DC-5200 Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-2501 Cosmetic Wax (Dimethicone Copolyol); DC-2502 Fluid (Cetyl Dimethicone); DC-2503 Wax (Stearyl Dimethicone); DC-1731 Volatile Fluid (Caproyl Trimethicone); DC-580 Wax (Stearoxytrimethylsilane [and] Stearyl Alcohol); DC-1-3563 (Dimethiconal); DC-X2-1286 (Dimethiconol); DC-X2-1146A (Cylcomethicone [and] Dimethiconol); DC-8820 Fluid (Amino functionalized); DC Q5-0158A wax (stearoxytrimethylsilane); DC-Q2-8220 (Trimethylsilylamodimethicone); DC-7224 (Trimethylsilylamodimethicone); DC-X2-1318 Fluid (Cyclomethicone [and] Vinyldimethicone); DC-QF1-3593A fluid (Trimethylsiloxysilicate) and combinations thereof.

Other nonlimiting examples of suitable modified silicone carriers for use in the antiperspirant compositions herein include the following modified silicones available from General Electric: GE SF-1023 (Dimethyl-Diphenyl-Siloxane); GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1328; GE SF-1188 (Dimethicone copolyol); GE SF-1188A (Silicone polyether copolymer); GE SF-1288 (silicone polyether copolymer, dimethyl-methyl 3-hydroxypropyl ethoxylated); GE SF-1318 (Methylester Siloxane); GE SF-1328 (silicone surfactant, dimethyl-methyl 3-hydroxypropyl ethoxylated-propoxylated); GE SF-1550 (methylphenyl siloxane, hexamethyl-3-phenyl-3-[[trimethylsilyl]oxy]trisiloxane); GE SF-1632 (silicone wax); GE SS-4267 (Dimethicone [and] Trimethylsiloxysilicate) and combinations thereof.

Other nonlimiting examples of suitable modified silicone carriers for use in the antiperspirant compositions herein include the following modified silicones available from Goldschmidt: Abil EM-90 (silicone emulsifier); Abil EM-97 (polyether siloxane); Abil Wax 9810 (silicone wax or C24-28 methicone); Abil Wax 2434 (Stearoxy Dimethicone); Abil Wax 9800D (Stearyl Dimethicone); Tegomer H—Si 2111, H—Si 2311, A—Si 2120, A—Si 2320, C—Si 2141, C—Si 2341, E—Si 2130, E—Si 2330, V—Si 2150, V—Si 2550, H—Si 6420, H—Si 6440, H—Si 6460 (Alpha-Omega Dimethicone Copolymers) and combinations thereof.

Other nonlimiting examples of suitable modified silicone carriers for use in the antiperspirant compositions herein include the following: Masil 756 from PPG Industries (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Silicone L-711, L-720, L-721 and L722 (dimethicone copolyols from Union Carbide); Silicone L-7000, L-7001, L-7002, L-7004, L-7500, L-7600, L-7602, L-7604, L-7605, and L-7610 (dimethicone copolyols from Union Carbide); Unisil SF-R (dimethiconol from UPI); Silicate Cluster from Olin (Tris[tributoxysiloxy] methylsilane); silicone copolymer F-754 (dimethicone copoly from SWS Silicones); and combinations thereof.

The antiperspirant composition of the present invention preferably comprises a volatile silicone carrier in combination with isopropyl glycerol ether. The concentration of the volatile silicone preferably range from about 10% to about 90%, more preferably from about 15% to about 65%, by weight of the antiperspirant composition. These volatile silicone carriers may be cyclic, linear or branched chain silicones having the requisite volatility defined herein. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicon atoms. Most preferably are those which conform to the formula:

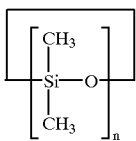

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V ( available from Mazer) and combinations thereof.

Optional liquid carriers may also include a non-volatile silicone carrier other than or in addition to the preferred modified silicone carriers described hereinbefore. These non-volatile silicone carriers are preferably linear silicones which include, but are not limited to, those which conform to either of the formulas:

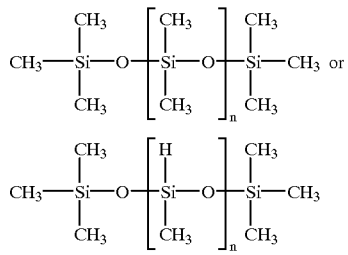

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the antiperspirant compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

The antiperspirant composition preferably comprises a combination of volatile and nonvolatile silicone materials, more preferably a combination of volatile and nonvolatile silicone carrier liquids. Nonlimiting examples of suitable combinations of such silicone materials are described in U.S. Pat. No. 5,156,834 (Beckmeyer et al.), which descriptions are incorporated herein by reference.

Optional liquid carriers for use in combination with the isopropyl glycerol ether may also include mono and polyhydric alcohols (e.g., 1,2-hexanediol), fatty acids, esters of mono and dibasic carboxylic acids with mono and polyhydric alcohols, polyoxyethylenes, polyoxypropylenes, polyalkoxylates ethers of alcohols, and combinations thereof. Preferably such optional liquid carriers are also water-immiscible liquids under ambient conditions. Other suitable water-immiscible, polar organic liquid carriers or solvents for use in combination with the isopropyl glycerol ether are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Other optional liquid carriers for use in combination with the isopropyl glycerol ether include anhydrous, water-miscible, polar organic liquid carriers or solvents, examples of which include short chain alcohols such as ethanol and glycol solvents such as propylene glycol, hexylene glyol, dipropylene glycol, tripropylene glycol, and so forth. Other suitable similar solvents also include polyalkoxylated carriers such as polyethylene glycols, polyproylene glycols, combinations and derivatives thereof, and so forth. Nonlimiting examples of polar solvents suitable for use herein are described in U.S. Pat. No. 5,429,816. Other suitable polar solvents include phthalate co-solvents, benzoate co-solvents, cinnamate esters, secondary alcohols, benzyl acetate, phenyl alkane and combinations thereof.

Optional liquid carriers for use in combination with the isopropyl glycerol ether may also include non-polar carriers such as mineral oil, petrolatum, isohexadecane, isododecane, various hydrocarbon oils such as the Isopar or Norpar series available from Exxon Corp. or Permethyl series available from Perperse, and the Soltrol series available from Phillips Chemical, and any other polar or non-polar, water-miscible, organic carrier liquid or solvent known or otherwise safe and effective for topical application to human skin.

Other optional liquid carriers for use in combination with the isopropyl glycerol ether includes fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress® PFPE oils, and the series fluorosurfactants from Dupont Performance Chemicals under the trade name Zonyl® Fluorosurfactants.

Antiperspirant Active

The antiperspirant compositions of the present invention comprise an antiperspirant active suitable for application to human skin. The actives may be solubilized in the composition or may be suspended as undissolved or precipitated solids. The concentration of antiperspirant active in the composition should be sufficient to provide the desired perspiration wetness and odor control.

The antiperspirant compositions of the present invention comprise antiperspirant active at concentrations of from about 0.1% to about 99.9%, preferably from about 0.5% to about 50%, more preferably from about 5% to about 35%, even more preferably from about 6% to about 26%, by weight of the composition. All such weight percentages are calculated on an anhydrous metal salt basis exclusive of water and any complexing agents such as glycine, glycine salts, or other complexing agents.

The antiperspirant active may be formulated as particulate solids in the form of dispersed solid particles having a preferred average particle size or diameter of less than about 100 μm, more preferably from about 15 μm to about 100 μm, even more preferably from about 20 μm to about 100 μm. Also preferred are dispersed solid particulates having an average particle size or diameter of less than about 2 μm, even more preferably from less than about 0.4 μm.

The antiperspirant active for use in the antiperspirant compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions include those which conform to the formula:

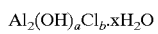

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant compositions include those which conform to the formula:

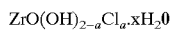

$$ZrO(OH)_{2-a}Cl_a \cdot xH_2O$$

wherein a is any number having a value of from about 0 to about 2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant compositions of the present invention can also be formulated to comprise other active materials in addition to or in place of the antiperspirant active described herein. Such other active materials can likewise be dissolve or suspended solids, and include any active material known or otherwise suitable for topical application to human skin, for example deodorant active and/or perfumes as described hereinafter.

The antiperspirant compositions of the present invention may comprise solubilized antiperspirant active, preferably solubilized antiperspirant active in an anhydrous system. The concentration of solubilized antiperspirant active in the composition preferably ranges from about 0.1% to 35%, more preferably from about 0.5% to about 25%, even more preferably from about 1% to about 17%, even more preferably from about 6% to about 17%, by weight of the antiperspirant composition (weight percentages calculated on an anhydrous metal salt basis exclusive of water and any complexing agents such as glycine, glycine salts, or other complexing agents). It has been found that such anhydrous compositions have good application and aesthetic characteristics, and with respect to other solubilized active compositions, are typically less sticky during or after application and are milder to the skin. It has also been found that solutions of solubilized antiperspirant active and isopropyl glycerol ether are more compatible with nonpolar solvents, even when the latter is used at higher concentrations. This now allows for the formulation of clear or translucent antiperspirant compositions containing nonpolar solvents such as volatile and nonvolatile silicones.

Suspending or thickening agent

The antiperspirant compositions of the present invention may further comprise a suspending or thickening agent to help provide the composition with the desired viscosity or product hardness, or to otherwise help suspend any dispersed solids or liquids within the composition. Suitable suspending or thickening agents include any material known or otherwise effective in providing suspending or thickening properties to the composition, or which otherwise provide structure to the final product form. These suspending or thickening agents include gelling agents, and polymeric or nonpolymeric or inorganic thickening or viscosifying agents. Such materials will most typically include organic solids, silicone solids, crystalline or other gellants, inorganic particulates such as clays or silicas, or combinations thereof.

The concentration and type of the optional suspending or thickening agent selected for use in the antiperspirant composition will vary depending upon the desired product form, viscosity, and hardness. For most suspending or thickening agents suitable for optional use herein, the concentration of such suspending or thickening agents will most typically range from about 0.1% to about 35%, more typically from about 0.1% to about 20%, by weight of the composition.

Suitable gelling agents for use as optional suspending or thickening agents in the antiperspirant composition include, but are not limited to, fatty acid gellants, hydroxy acid gellants, esters and amides of fatty acid or hydroxy fatty acid gellants, cholesterolic materials, dibenzylidene alditols, lanolinolic materials, and other amide and polyamide gellants.

Suitable gelling agents include fatty alcohols having from about 8 to about 40 carbon atoms, preferably from 8 to about 30 carbon atoms, more preferably from about 12 to about 18 carbon atoms. These gelling agents are wax-like materials which are most typically used at concentrations ranging from about 1% to about 25%, preferably from about 5% to about 20%, most preferably from about 10% to about 20%, by weight of the antiperspirant composition. Preferred are cetyl alcohol, myristyl alcohol, stearyl alcohol and combinations thereof, more preferably stearyl alcohol.

Other suitable gelling agents include waxes or wax-like materials having a melt point of above 65° C., more typically from about 65° C. to about 130° C., examples of which include, but are not limited to, waxes such as beeswax, carnauba, baysberry, candelilla, montan, ozokerite, ceresin, hydrogenated castor oil (castor wax), synthetic waxes, microcrystalline waxes. Castor wax is preferred within this group. Other high melting point waxes are described in U.S. Pat. No. 4,049,792, Elsnau, issued Sep. 20, 1977, which description is incorporated herein by reference.

Other suitable gelling agents include fatty acid gellants such as fatty acid and hydroxy or alpha hydroxy fatty acids, having from about 10 to about 40 carbon atoms, and esters and amides of such gelling agents. Non-limiting examples such gelling agents include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred are 12-hydroxystearic acid, esters of 12-hydroxystearic acid, amides of 12-hydroxystearic acid and combinations thereof, and all other gelling agents which correspond to the following formula:

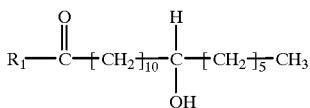

wherein $R_1$ is $OR_2$, $NR_2R_3$, or a silicone containing moiety; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Suitable amide gellants include disubstituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, apartic acid, and combinations thereof. Other suitable amide gelling agents are described in U.S. Pat. No. 5,429,816, issued Jul. 4, 1995, and U.S. patent application Ser. No. 08/771,183, filed Dec. 20, 1996, which descriptions are incorporated herein by reference. Concentrations of all such gelling agents preferably range from about 0.1% to about 25%, preferably of from about 1% to about 15%, more preferably from about 1% to about 10%, by weight of the antiperspirant composition.

Other suitable gelling agents include triglyceride gellant systems which comprise glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant material preferably has a melting point of at less than about 110° C., preferably between about 50° C. and 110° C.

Preferred concentrations of the above-described triglyceride gellant systems range from about 0.1% to about 20%, more preferably from about 0.5% to about 15%, by weight of the antiperspirant composition. For roll-on formulations having a penetration force value of from about 20 gram-force to about 100 gram-force, triglyceride concentrations preferably range from about 1% to about 5% by weight of the antiperspirant composition. For other cream formulations, including those formulations suitable for use in cream applicator devices, which have a penetration force value of from about 100 gram-force to about 500 gram-force, triglyceride concentrations preferably range from about 4% to about 20%, more preferably from about 4% to about 10%, by weight of the antiperspirant composition. Specific examples of triglyceride gelling agents for use in the antiperspirant compositions that are commercially available include, but are not limited to, tristearin, hydrogenated vegetable oil, trihydroxysterin (Thixcin® R, available from Rheox, Inc.), rape seed oil, castor wax, fish oils, tripalmiten, Syncrowax® HRC and Syncrowax® HGL-C (Syncrowax® available from Croda, Inc.).

Other suitable suspending or thickening agents for use in the antiperspirant composition include particulate suspending or thickening agents such as clays and colloidal pyrogenic silica pigments. Other known or otherwise effective particulate suspending or thickening agents can likewise be used in the antiperspirant composition. Concentrations of optional particulate thickening agents preferably range from about 0.001% to about 15%, more preferably from about 1% to about 15%, even more preferably from about 1% to about 8%, by weight of the composition. Colloidal pyrogenic silica pigments are preferred, a common example of which includes Cab-O-Sil®, a submicroscopic particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Non-limiting examples of suitable clay activators include propylene carbonate, ethanol, and combinations thereof. The amount of clay activator will typically range from about 25% to about 75% by weight of the clay, more typically from about 40% to about 60% by weight of the clay.

Optional Deodorant Active and Fragrance

The antiperspirant compositions of the present invention may further comprise a deodorant active, fragrance or combination thereof at concentrations ranging from about 0.001% to about 50%, preferably from about 0.01% to about 20%, more preferably from about 0.1% to about 10%, by weight of the composition. These deodorant actives and perfumes may be used in addition to or in place of some or all of the antiperspirant active material, and include any known or otherwise safe and effective deodorant or fragrance suitable for topical application to human skin.

Deodorant actives suitable for use in the composition of the present invention includes any topical material that is known for or is otherwise effective in preventing or eliminating malodor associated with perspiration, other than those active materials described hereinbefore. These deodorant actives are typically antimicrobial agents (e.g., bacteriocides, fungicides), malodor-absorbing material, or combinations thereof.

Preferred deodorant actives are antimicrobial agents, nonlimiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether, 3,4,4'-trichlorocarbanilide, diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Other optional deodorant actives include odor-absorbing materials such as carbonate and bicarbonate salts, including alkali metal carbonates and bicarbonates, ammonium and tetraalkylammonium Preferred are sodium and potassium salts of such odor-absorbing materials.

The antiperspirant composition of the present invention may optionally comprise fragrances suitable for use in a topical composition, and includes any topical material that is known for or is otherwise effective in masking malodor associated with perspiration, or which otherwise provides the composition with the desired perfumed aroma. These fragrances include any perfume or perfume chemical suitable for topical application to the skin.

The concentration of the optional fragrance should be effective to provide the desired aroma characteristics or to mask malodor, wherein the malodor is inherently associated with the composition itself or is associated with malodor development from human perspiration. Also, the fragrance and whatever carriers accompany it preferably do not impart excessive stinging to the skin, especially broken or irritated skin, at the levels previously disclosed. The fragrance will typically be in the form of water insoluble perfumes that are solubilized in the matrix of the composition.

Fragrances are made by those skilled in the art in a wide variety of fragrances and strengths. Typical fragrances are described in Arctander, Perfume and Flavour Chemicals (Aroma Chemicals), Vol. I and II (1969); and Arctander, Perfume and Flavour Materials of Natural Origin (1960). U.S. Pat. No. 4,322,308 and U.S. Pat. No. 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-annelid-1:4). Fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

Other suitable but optional fragrances are those which mask or help to mask odors associated with perspiration (hereinafter referred to as odor masking fragrances), some nonlimiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The optional fragrance may also contain solubilizers, diluents, or solvents which are well known in the art. Such materials are described in Arctander, Perfume and Flavour Chemicals (Aroma Chemicals), Vol. I and II (1969). These materials typically include dipropylene glycol, diethylene glycol, $C_1$–$C_6$ alcohols (other than 1,2-hexandiol), and benzyl alcohol.

Optional Ingredients

The antiperspirant compositions of the present invention may further comprise one or more optional components which may modify the physical, chemical, cosmetic or aesthetic characteristics of the compositions or serve as additional "active" components when deposited on the skin. The compositions may also further comprise optional inert ingredients. Many such optional ingredients are known for use in deodorants, antiperspirants or other personal care compositions, and may also be used in the antiperspirant compositions herein, provided that such optional materials are compatible with the essential materials described herein, or do not otherwise unduly impair product performance.

Nonlimiting examples of optional ingredients suitable for use in the antiperspirant compositions herein include pH buffering agents; additional emollients; humectants; soothing agents; dyes and pigments; medicaments; baking soda and related materials, preservatives; and soothing agents such as aloe vera, allantoin, D-panthenol, avocado oil and other vegetative oils, and lichen extract.

Skin Irritation

It has been found that solutions of solubilized antiperspirant active and isopropyl glycerol ether are less irritating to the skin than other similar compositions, including deodorant compositions containing propylene glycol and dipropylene glycol as described hereinafter. To emphasize this benefit, the compositions described in Table I are evaluated for skin irritation in a three day patch test. Skin irritation potential is measured by visual grading of skin erythema (redness) by qualified skin graders using a 0 (no apparant skin irritation) to 4 (severe skin irritation) grading scale. Data are reported as a least square mean average (LS mean score) of 21 panelists with statistics.

TABLE 1

| Composition | LS mean score | Statistical grouping |
| --- | --- | --- |
| A 25% active + 75% isopropyl glyerol ether | 0.083 | a |
| B Commercial deodorant containing about 20% propylene glycol + 40% dipropylene | 0.50 | b |

The data set forth in Table I shows that compositions containing antiperspirant active solubilized in 75% isopropyl glycerol ether are less irritating (statistically significant at 90% confidence) to the skin than deodorant compositions containing at total of about 60% polyhydric alcohols (about 20% propylene glycol and about 40% dipropylene glycol).

Method of Manufacture

The compositions of the present invention may be made by any of the methods known in the art for formulating antiperspirant compositions, or which are otherwise effective in formulating such compositions. As will be apparent to those skilled in the art, the particular method will be dependent upon the selection of the specific types and amounts of the components employed, as well as the final product form desired, e.g., liquids, sticks, soft solids, creams, lotions, single or multiple phase systems containing solid or dissolved antiperspirant active, suspensions or solutions, clear or translucent or opaque, etc.

In general, the antiperspirant compositions of the present invention can be prepared by merely combining the liquid carrier with the antiperspirant active. Optional ingredients can be added in any known or otherwise effective matter for formulating the desired product form.

For example, to formulate an anhydrous composition containing solubilized antiperspirant active, the antiperspirant active may be solubilized in an aqueous carrier comprising a polyol solvent, wherein the polyol solvent is or comprises isopropyl glycerol ether, and then processed to remove substantially all of the water in the resulting composition. Suitable processing methods for application in this manner include those methods described in U.S. Pat. No. 4,781,917 (Luebbe et al.), U.S. Pat. No. 5,643,558 (Provancal et al.), and European Patent Application 0 404 533 A1 (Smith et al.), which descriptions are incorporated herein by reference.

To formulate a solid or soft solid stick, the liquid carrier is combined with an optional suspending agent. The combination is heated until it appears to be clear and homogenous, which will typically occur for most combinations at a temperature of between about 60° C. and about 130° C. The resulting clear liquid is cooled or allowed to cool to between about 40° C. and about 120° C. at which time the solid or solubilized antiperspirant active is added to and thoroughly mixed in the clear liquid along with any other optional ingredients. The resulting liquid mixture is then poured into containers and allowed to cool and solidify to the desired product hardness. Alternatively, the antiperspirant active or other optional ingredients can be added along with the liquid carrier and the optional suspending agent, or at any other time that is suitable for such addition in order to manufacture the desired product form.

To formulate an aerosol, roll-on or other liquid formulation, any known or otherwise effective manufacturing or formulation method can be use to formulate the antiperspirant compositions in such product forms.

Nonlimiting examples of suitable methods for manufacturing the antiperspirant compositions of the present invention are described in U.S. Pat. No. 5,429,816 (Hofrichter et al.); U.S. Pat. No. 5,733,534 (Sawin et al.); U.S. Pat. No. 5,605,681 (Trandai et al.); U.S. Pat. No. 5,346,694 (Juneja); U.S. Pat. No. 5,298,236 (Orr et al.); and U.S. Pat. No. 5,718,890 (Putnam et al.), which descriptions are incorporated herein be reference.

Method For Use

The antiperspirant composition of the present invention may be used as an intermediate in formulating other antiperspirant compositions, or it may be formulated in final form to be topically applied to the axilla or other area of the skin in any known or otherwise effective method for controlling malodor associated with perspiration. These methods comprise applying to the axilla or other area of the human skin a safe and effective amount of the antiperspirant composition of the present invention. In this context, the term "safe and effective amount" means an amount of the antiperspirant composition topically applied to the skin which is effective in inhibiting or minimizing masking, perspiration at the site of application while also being safe for human use at a reasonable risk/benefit ratio. In this context, a safe and effective amount typically ranges from about 0.1 gram per axilla to about 2.0 gram per axilla. The compositions are preferably applied to the axilla or other area of the skin one or more times daily, preferably once daily.

EXAMPLES

The following Examples 1–12 illustrate specific embodiments of the antiperspirant compositions of the present invention, including methods of manufacture and use, but are not intended to be limiting thereof. Other modifications can be undertaken by the skilled artisan without departing from the spirit and scope of this invention.

Each of the exemplified compositions is applied topically to the underarm in an amount effective to inhibit or prevent perspiration in humans, typically an amount which ranges from about 0.1 gram to about 2 grams per axilla. The applied compositions are effective in inhibiting perspiration from the applied areas, and have good skin feel characteristics during and after application. The applied compositions are milder to the skin and cause little or no skin irritation. All exemplified amounts are weight-weight percents based on the total weight of the composition, unless otherwise specified.

The antiperspirant compositions described in Examples 1–7 contain solubilized antiperspirant active, whereas the antiperspirant compositions described in Examples 8–13 contain solid antiperspirant active.

Examples 1–7

The antiperspirant compositions of the present invention includes the clear or translucent liquid compositions (Examples 1–7) as described below. Each contains solubilized antiperspirant active and is formulated by methods well known for making solubilized antiperspirant active or product forms containing them. These compositions may be applied topically to the skin, or they may be used as intermediates in formulating other antiperspirant product forms which contain solubilized antiperspirant active.

TABLE 2

| Ingredient | Examples | | | | | | |
|---|---|---|---|---|---|---|---|
| | 1 | 2 | 3 | 4 | 5 | 6 | 7 |
| Aluminum zirconium trichlorhydrex glycinate | 1 | 5 | 25 | 66 | 1 | 10 | 16 |
| isopropyl glycerol ether | 99 | 95 | 75 | 34 | 72 | 58 | 32 |
| Cyclomethicone D5 | — | — | — | — | 21 | 20 | 32 |
| Dimethiconol | — | — | — | — | 6 | 12 | 20 |

Example 8

The antiperspirant compositions of the present invention includes the gel solid stick composition described below. The gel solid stick contains solid antiperspirant active and is formulated in accordance with the methods described in U.S. Pat. No. 5,429,816.

| Ingredient | Concentration |
|---|---|
| Aluminum zirconium trichlorohydrex glycinate | 26 |
| Isopropyl glycerol ether | 10 |
| cyclomethicone D5 | 40 |
| 12-hydroxysteric acid | 7 |
| Dibutyl lauroyl glutamide | 2 |
| Dimethiconol | 2 |
| Cetearyl alcohol | 2 |
| Isopar M | 10 |
| Perfume | 1 |

Example 9

The antiperspirant compositions of the present invention includes the solid stick embodiment described below. The solid stick is formulated by methods well known for preparing antiperspirant sticks.

| Ingredient | Concentration |
|---|---|
| Aluminum zirconium trichlorohydrex glycinate | 26 |
| Isopropyl glycerol ether | 5 |
| Cyclomethicone D5 | 31 |
| Dimethiconol | 10 |
| Stearyl alcohol | 20 |
| Hydrogenated castor oil | 2 |
| Talc | 5 |
| Silica | 1 |

Example 10

The antiperspirant compositions of the present invention include the roll-on embodiment described below. The roll-on embodiement is formulated by methods well known for preparing liquid or roll-on antiperspirant compositions, and is contained within a suitable roll-on package.

| Ingredient | Concentration |
|---|---|
| Aluminum zirconium trichlorohydrex glycinate | 26 |
| Isopropyl glycerol ether | 20 |
| Cyclomethicone D5 | 40 |
| Dimethiconol | 10 |
| Silica | 2.0 |
| Perfume | 2.0 |

Example 11

The antiperspirant compositions of the present invention includes the aerosol embodiment described below. It is formulated by methods well known for preparing aerosolized antiperspirant compositions, and is contained within a suitable aerosolized package.

| Ingredient | Concentration |
|---|---|
| Aluminum chlorohydrate | 15 |
| Isopropyl glycerol ether | 5 |
| Cyclomethicone D5 | 20.34 |
| Isopropyl myristate | 4 |
| Dimethiconol | 10 |
| Quaternium-18 hectorite | 2 |
| Propellant | 43 |
| Propylene carbonate | 0.66 |

The aerosol antiperspirant composition of Example 11 is an embodiment of the present invention which can be topically applied to the underarm and causes minimal or no skin irritation. It has a dry feel during and after application and does not leave a sticky residue on the underarm.

Example 12

The antiperspirant compositions of the present invention includes the soft solid or cream embodiment described below. It is formulated in accordance with the methods described in U.S. Pat. No. 5,718,890 (Putnam et al.), and is contained within the perforated dome packages described in the Putnam et al. patent.

| Ingredient | Concentration |
|---|---|
| Aluminum zirconium trichlorohydrex glycinate | 26 |
| Isopropyl glycerol ether | 14 |
| Cyclomethicone D5 | 30 |
| Tribehenen | 20 |
| C18-36 acid triglyceride | 9 |
| Perfume | 1 |

What is claimed is:
1. An antiperspirant composition comprising:
A) from about 0.1% to about 99.9% by weight of isopropyl glycerol ether; and

B) from about 0.1% to about 99.9% by weight of an antiperspirant active.

2. The antiperspirant composition of claim 1 wherein the composition comprises from about 0.1% to about 35% by weight of solubilized antiperspirant active.

3. The antiperspirant composition of claim 2 wherein the composition is visibly clear or translucent at 25° C.

4. The antiperspirant composition of claim 1 wherein the composition comprises from about 0.1% to about 35% by weight of solid antiperspirant active.

5. The antiperspirant composition of claim 1 wherein the composition comprises from about 0.1% to about 70% by weight of isopropyl glycerol ether.

6. The antiperspirant composition of claim 5 wherein the composition comprises from about 1% to about 40% by weight of isopropyl glycerol ether.

7. The antiperspirant composition of claim 5 wherein the composition further comprises from about 1% to about 35% by weight of dimethiconol.

8. The antiperspirant composition of claim 7 wherein the dimethiconol is represented by the formula

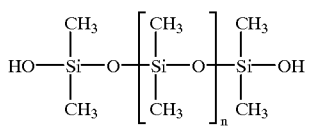

wherein n is a number having a value of from 0 to about 20.

9. The antiperspirant composition of claim 1 wherein the composition further comprises about 10% to about 90% by weight of a volatile silicone carrier liquid.

10. The antiperspirant composition of claim 9 wherein the composition further comprises a nonvolatile silicone.

11. The antiperspirant composition of claim 1 wherein the composition is anhydrous and contains less than 3% by weight of free or added water.

12. The antiperspirant composition of claim 1 wherein the antiperspirant active is selected from the group consisting of aluminum salts, zirconium salts, and combinations thereof.

13. An antiperspirant composition comprising:
A) from about 0.5% to about 50% by weight of an antiperspirant active;
B) from about 0.1% to about 35% by weight of a suspending or thickening agent; and
C) from about 10% to about 90% by weight of a liquid carrier containing isopropyl glycerol ether.

14. The antiperspirant composition of claim 13 wherein the composition comprises from about 0.5% to about 25% by weight of solubilized antiperspirant active.

15. The antiperspirant composition of claim 13 wherein the composition comprises from about 0.5% to about 35% by weight of solid antiperspirant active.

16. The antiperspirant composition of claim 13 wherein the composition comprises from about 0.1% to about 70% by weight of isopropyl glycerol ether.

17. The antiperspirant composition of claim 16 wherein the composition comprises from about 1% to about 40% by weight of isopropyl glycerol ether.

18. The antiperspirant composition of claim 13 wherein the liquid carrier further comprises a volatile silicone carrier.

19. The antiperspirant composition of claim 18 wherein the liquid carrier further comprises a volatile silicone and a nonvolatile silicone.

20. The antiperspirant composition of claim 14 wherein the composition further comprises a volatile silicone and a nonvolatile silicone.

21. The antiperspirant composition of claim 14 wherein the suspending or thickening agent is an organic solid.

22. The antiperspirant composition of claim 14 wherein the suspending or thickening agent is a silicone solid.

23. The antiperspirant composition of claim 14 wherein the suspending or thickening agent is an inorganic particulate.

24. The antiperspirant composition of claim 14 wherein the composition is anhydrous and contains less than 5% by weight of free or added water.

25. The antiperspirant composition of claim 14 wherein the composition further comprises an odor masking fragrance having a Deodorant Value of at least about 0.25.

26. An antiperspirant composition comprising:
A) from about 0.5% to about 50% by weight of an antiperspirant active;
B) from about 0.1% to about 35% by weight of a suspending or thickening agent;
C) from about 10% to about 90% by weight of a liquid carrier containing isopropyl glycerol ether and dimethiconol.

27. The antiperspirant composition of claim 26 wherein the composition comprises from about 1% to about 35% by weight of the dimethiconol and from about 1% to about 40% by weight of the isopropyl glycerol ether.

28. The antiperspirant composition of claim 26 wherein the dimethiconol is represented by the formula

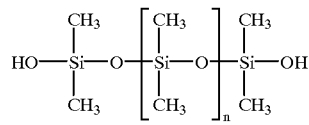

wherein n is a number having a value of from 0 to about 20.

29. The antiperspirant composition of claim 26 wherein the composition comprises from about 0.5% to about 35% by weight of solubilized antiperspirant active.

30. The antiperspirant composition of claim 26 wherein the composition comprises from about 0.5% to about 35% by weight of solid antiperspirant active.

31. The antiperspirant composition of claim 29 wherein the liquid carrier further comprises a volatile silicone carrier liquid.

32. The antiperspirant composition of claim 29 wherein the liquid carrier further comprises a volatile silicone carrier liquid and a nonvolatile silicone carrier liquid.

33. The antiperspirant composition of claim 29 wherein the suspending or thickening agent is an organic solid.

34. The antiperspirant composition of claim 29 wherein the suspending or thickening agent is a silicone solid.

35. The antiperspirant composition of claim 29 wherein the suspending or thickening agent is an inorganic particulate.

36. The antiperspirant composition of claim 29 wherein the composition is anhydrous and contains less than 3% by weight of free or added water.

37. The antiperspirant composition of claim 29 wherein the antiperspirant active is selected from the group consisting of aluminum salts, zirconium salts, and combinations thereof.

38. A method of controlling malodor associated with perspiration comprising the topical application to the axillary area of an effective amount of the antiperspirant composition of claim 13.

39. A method of controlling malodor associated with perspiration comprising the topical application to the axillary area of an effective amount of the antiperspirant composition of claim 26.

* * * * *